United States Patent [19]

Rodder

[11] 4,109,510
[45] Aug. 29, 1978

[54] FLUID MEASURING APPARATUS

[76] Inventor: Jerome A. Rodder, 774 Sunshine Dr., Los Altos, Calif. 94022

[21] Appl. No.: 787,468

[22] Filed: Apr. 14, 1977

[51] Int. Cl.² .................. G01N 27/04; G01F 1/68
[52] U.S. Cl. .................................. 73/27 R; 73/204
[58] Field of Search ............. 73/27 R, 204; 338/34, 338/318

[56] References Cited

U.S. PATENT DOCUMENTS

| | | | |
|---|---|---|---|
| 2,269,850 | 1/1942 | Hebler | 73/27 R |
| 2,619,409 | 11/1952 | Spracklen | 73/27 R |
| 3,084,536 | 4/1963 | McNabb | 73/27 R |
| 3,474,660 | 10/1969 | Dooley | 73/27 R |
| 3,704,984 | 12/1972 | Kiefer | 73/27 R |
| 3,888,110 | 6/1975 | Clark | 73/27 R |
| 3,971,247 | 7/1976 | Rodder | 73/27 R |

FOREIGN PATENT DOCUMENTS 855,615  12/1960  United Kingdom .................. 73/27 R

*Primary Examiner*—Richard C. Queisser
*Assistant Examiner*—Stephen A. Kreitman
*Attorney, Agent, or Firm*—Christie, Parker & Hale

[57] ABSTRACT

A housing has elongated cavities in which four hot wires forming the arms of a bridge are disposed. Each hot wire comprises a first segment bent in half to extend along the length of the cavity away from a junction, and a second segment bent in half to extend along the length of the cavity away from the junction in the opposite direction from the first segment. The junction is centrally located relative to the ends of the cavity. The first and second segments are electrically connected to each other at one end and are electrically connected to other hot wires in the bridge at the other end by a printed circuit board at the junction. The middle of each segment is wrapped around first and second closely spaced rods deformed to exert tension on the segment. The circuit board is located in a chamber having a larger cross section than the cavities. In using the apparatus for chromatography, unknown gases in a carrier enter one of the cavities near the chamber. A reference gas enters the chamber to prevent the unknown gases from flowing to the chamber. The gases exit from the ends of the cavity.

19 Claims, 6 Drawing Figures

FLUID MEASURING APPARATUS

BACKGROUND OF THE INVENTION

This invention relates to sensitive, fast responding fluid measuring apparatus and, more particularly, to an improved hot wire anemometer.

In a hot wire anemometer, the hot wire is connected to serve as one arm of an electrical bridge circuit. Current passing through the hot wire heats the wire, thereby increasing its resistance. The hot wire is disposed in an elongated cavity through which the gas to be measured flows and cools the hot wire accordingly. If the type of gas passing through the cavity is known, the resistance change of the hot wire is a measure of the gas flow rate. If the flow rate of the gas passing through the cavity is known, the resistance change of the hot wire is a measure of the thermal conductivity of the gas and, hence, the gas type.

My U.S. Pat. No. 3,971,247, which issued July 27, 1976, discloses a thin elongated hot wire bent in half to extend along the length of a cavity formed in a housing. The ends of the hot wire are soldered to pads on a printed circuit board located at one end of the cavity for support and electrical connection to a bridge circuit. The middle of the hot wire is wrapped around a rod at the other end of the cavity for support. The rod is deformed to exert tension on the hot wire as its length changes. Thus, for a cavity having a given length, the length of the hot wire can be doubled and a corresponding increase in sensitivity can be achieved. But, the probability of a short circuit by contact between halves of the hot wire or the hot wire and the sides of the cavity rises, as the length of the cavity increases.

SUMMARY OF THE INVENTION

According to one feature of the invention, first and second thin elongated hot wires are bent in half to extend along the length of an elongated cavity away from a junction. The ends of each hot wire are supported at the junction in spaced, electrically isolated relationship from each other and from the sides of the cavity. The middle of each hot wire is supported by a spring exerting tension thereon as the length of the hot wire changes. The hot wires are electrically connected to each other at one end. At the other end, the hot wires are electrically connected to a bridge. As a result, the first and second hot wires form in effect a single hot wire equal in length to the first and second hot wires, and the sensitivity is increased accordingly. Preferably, the junction is centrally located relative to the ends of the cavity so the first hot wire extends from the junction in one direction and the second hot wire extends from the junction in the direction opposite to the first hot wire. A fluid enters the cavity at the junction and exits the cavity at its ends. Consequently, one half of the fluid flows past each hot wire, which further increases the effective ratio of hot wire length to cavity volume.

One aspect of the invention is the use of hot wires in all four of the arms of a bridge. Two of the hot wires serve as a reference and the remaining two hot wires contribute to the bridge output signal in push-pull fashion. This further increases the sensitivity of the apparatus. In the preferred embodiment, the two fluid measuring wires are arranged in side-by-side relationship in a single cavity, and the two reference wires are arranged in closely spaced relationship in a single cavity.

According to another feature of the invention, the middle of a hot wire bent in half is supported by two side-by-side rods, which are deformed to exert tension on the hot wire as its length changes. This permits the spacing between the two halves of the wire to be controlled. For example, by proper spacing of the rods, the two halves of the hot wire can be maintained in precise parallel relationship, to minimize the probability of a short circuit.

Another aspect of the invention involves the use of the invention for chromatography. The ends of a hot wire bent in half to extend along the length of a cavity are supported in a chamber having, of necessity, a larger cross section than the cavity. One or more unknown gases in a carrier are introduced into the cavity near the chamber, and a reference gas is introduced into the chamber to prevent the one or more unknown gases from flowing toward the chamber. The gases exit the cavity at a point spaced from the chamber in the path of the hot wire. This arrangement prohibits the chamber from causing the pulses generated in response to the one or more unknown gases from spreading and merging with each other.

BRIEF DESCRIPTION OF THE DRAWING

The features of specific embodiments of the best mode contemplated for carrying out the invention are illustrated in the drawing, in which.

DETAILED DESCRIPTION OF THE SPECIFIC EMBODIMENTS

The disclosure of my U.S. Pat. No. 3,971,247, which issued July 27, 1976, is incorporated herein by reference.

Figure 1:
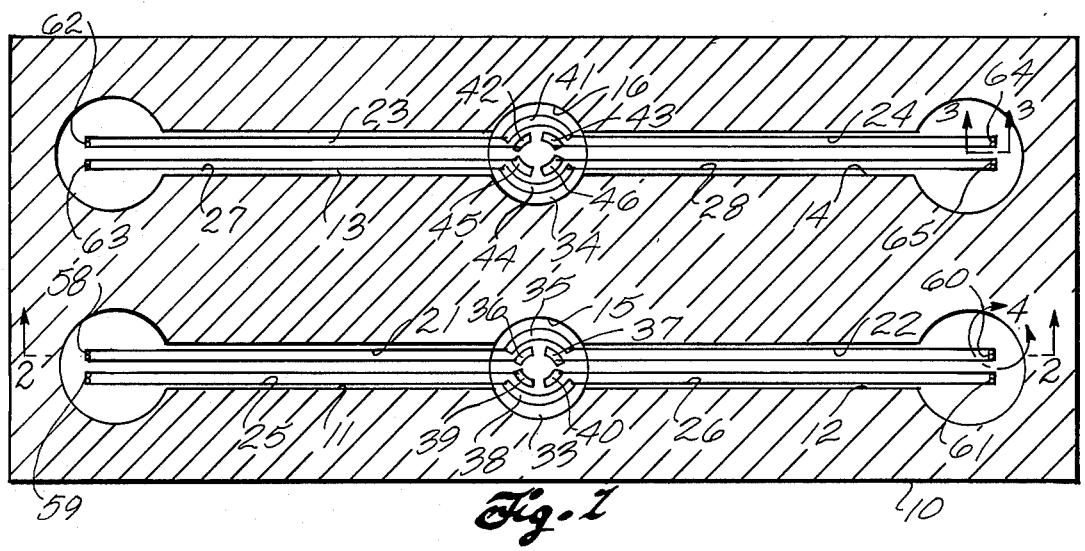
FIG. 1 is a top sectional view of fluid measuring apparatus incorporating principles of the invention.
Figure 2:
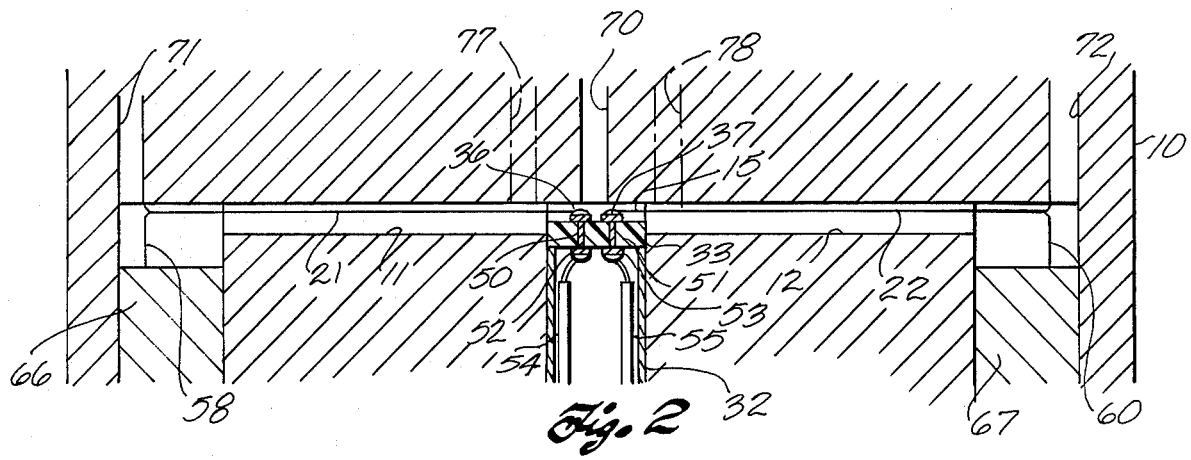
FIG. 2 is a side sectional view of the apparatus of FIG. 1.

In FIGS. 1 and 2 is shown fluid measuring apparatus having a housing 10 made of a material having high thermal conductivity such as aluminum or steel to make the apparatus thermally stable. Parallel elongated cavities 11, 12, 13 and 14 are formed in housing 10. If desired, housing 10 could comprise a block having a surface in which the cavities are formed as grooves and a plate covering the surface to enclose the cavities as disclosed in my above referenced patent. Cavities 11 and 12 extend in axial alignment in opposite directions from a cylindrical chamber 15 in housing 10. Similarly, cavities 13 and 14 extend in axial alignment in opposite directions from a cylindrical chamber 16 in housing 10. Chambers 15 and 16 have cylindrical axes transverse to the axes of cavities 11 through 14. Thin elongated, i.e., uncoiled, hot wires 21 and 22, which are bent in half, extend along the length of cavities 11 and 12, respectively; similarly, thin elongated hot wires 25 and 26, which are bent in half, also extend along the length of cavities 11 and 12, respectively. Thin elongated hot wires 23 and 24, which are bent in half, extend along the length of cavities 13 and 14, respectively; thin elongated hot wires 27 and 28, which are bent in half, also extend along the length of cavities 13 and 14, respectively.

Circular, disc-shaped printed circuit boards 33 and 34 for supporting and electrically connecting the ends of the hot wires fit in chambers 15 and 16, respectively. As illustrated by tube 32 for printed circuit board 33, each printed circuit board (33, 34) is attached to the end of a tube that is rotatable and translatable within its chamber (15, 16). This permits minor adjustments in the alignment of the hot wire. Because of the space requirements of printed circuit boards 33 and 34, chambers 15 and 16 have of necessity a larger cross section, i.e., diameter, than cavities 11 through 14.

Each printed circuit board has an electrically insulative substrate on which electrically conductive, coaxial arcuate pads are deposited. Solder connections are formed between the pads and the ends of the hot wires. Circuit board 33 has a long pad 35 interconnecting hot wires 21 and 22 at one end to form, in effect, a single hot wire $R_1$ equal in length to hot wires 21 and 22. At the other end, hot wire 21 is connected to a short pad 36 and hot wire 22 is connected to a short pad 37. At one end, hot wires 25 and 26 are interconnected by a long pad 38 to form in effect a single hot wire $R_2$ equal in length to hot wires 25 and 26. At the other end, hot wire 25 is connected to a short pad 39 and hot wire 26 is connected to a short pad 40. Circuit board 34 has a long pad 41 interconnecting hot wires 23 and 24 at one end to form, in effect, a single hot wire $R_3$ equal in length to hot wires 23 and 24. At the other end, hot wire 23 is connected to a short pad 42 and hot wire 24 is connected to a short pad 43. At one end, hot wires 27 and 28 are interconnected by a long pad 44 to form in effect a single hot wire $R_4$ equal in length to hot wires 27 and 28. At the other end, hot wire 27 is connected to a short pad 45 and hot wire 28 is connected to a short pad 46.

As shown in FIG. 2 for circuit board 33, the short pads are electrically connected by plated through holes, such as those designated 50 and 51 for pads 36 and 37, respectively, to pads, such as those designated 52 and 53, on the underside of circuit board 33. Large insulated wires, such as those designated 54 and 55, are soldered to the pads on the underside of the circuit boards to electrically connect the described hot wires in an electrical bridge, as described below in connection with FIG. 5. Wires 54 and 55 pass through tube 32.

Figure 3:
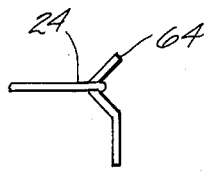
FIG. 3 is an enlarged side sectional view of a portion of the apparatus of FIG. 1 showing a hot wire supporting rod in detail.
Figure 4:
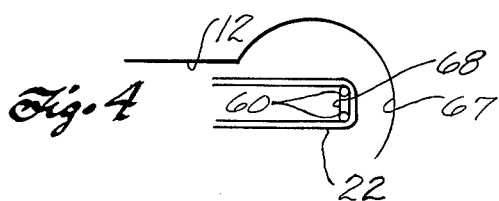
FIG. 4 is an enlargement of a portion of FIG. 1 showing the two spaced hot wire supporting rods in detail.

Pairs of rods 58 and 59 are located near the end of cavity 11 opposite chamber 15; pairs of rods 60 and 61 are located near the end of cavity 12 opposite chamber 15; pairs of rods 62 and 63 are located near the end of cavity 13 opposite chamber 16; and pairs of rods 64 and 65 are located near the end of cavity 14 opposite chamber 16. Rod pairs 58 through 65 are made of a nonconductive, resilient material such as quartz. As shown in FIG. 2 for rod pairs 58 and 60, each rod pair is anchored at one end in a rotatable and translatable cylindrical plug, such as those designated 66 and 67, and is free to move at the other end. The two rod pairs near each cavity end are offset from the diameter of the corresponding plug as depicted in FIG. 1. To make minor adjustments in the alignment of the hot wires, the plugs are rotated and translated slightly. As illustrated for rod pair 60 in FIG. 4, the spacing between rods is maintained by a strut 68 that is integral with each rod pair at the free end. The middle of the corresponding hot wire is wrapped around the free end of the pair of rods, as illustrated by hot wire 22 for rod pair 60 in FIG. 4. As illustrated in FIG. 3 for rod pair 64, each rod has a hook at its free end, which captures the hot wire and prevents its lateral movement. The free end of each rod pair is deformed, i.e., deflected, toward the corresponding circuit board so such rod functions as a spring to exert tension on the middle of the hot wire to keep the hot wire taut as its length changes. Preferably, the rods of each pair are spaced apart a distance that maintains the two halves of the corresponding hot wire precisely parallel to each other. The parallel relationship between hot wire halves reduces the probability of a short circuit and provides more uniform heating along the length of the hot wire, which permits greater sensitivity.

Cavities 11 and 12 form in effect a single long cavity with a centrally located junction where circuit board 15 supports and electrically connects the ends of hot wires $R_1$ and $R_2$; these hot wires are bent in half to extend in both directions from the junction to the ends of such cavity where the middle of each hot wire is wrapped around a rod pair. Similarly, cavities 13 and 14 form in effect a single long cavity with a centrally located junction.

The probability of hot wires becoming short circuited by touching each other or the sides of the cavities is reduced by the use of a pair of rods rather than a single rod and by the shorter distance between hot wire supports, which results by in effect placing the circuit board in the middle of each hot wire rather than at one end thereof. Further, the total gas flow is divided between two paths so only one half of the total gas flows past one half of each hot wire. This further reduces the probability of short circuiting due to hot wire vibration, which is caused by high gas flow rates.

A conduit 70 in housing 10 leads to chamber 15 to form an entrance for fluid to be measured. Conduits 71 and 72 in housing 10 lead from the ends of cavities 11 and 12, respectively, opposite chamber 15, to form exits for fluid to be measured. Hot wires 21 and 25 lie between entrance conduit 70 and exit conduit 71 in the path of gas flow through cavity 11. Similarly, hot wires 22 and 26 lie between entrance conduit 70 and exit conduit 72 in the path of gas flow through cavity 12.

Figure 5:
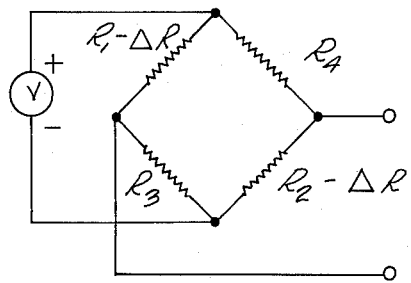
FIG. 5 is an electrical schematic diagram depicting the electrical connections of the hot wires in the apparatus of FIG. 1.

As shown in FIG. 5, hot wires $R_1$ and $R_3$ are connected in series between the output terminals of a voltage source V, with $R_1$ connected to the positive output terminal and hot wire $R_3$ connected to the negative output terminal. Hot wires $R_4$ and $R_2$ are connected in series between the output terminals of voltage source V, with hot wire $R_4$ connected to the positive output terminal and hot wire $R_2$ connected to the negative output terminal. The output of the bridge appears between the junction of hot wires $R_1$ and $R_3$ and the junction of hot wires $R_4$ and $R_2$. Because two arms of the bridge have hot wires, namely, $R_1$ and $R_2$, cooled by the gas to be measured, such hot wires operate in push-pull relationship to produce a bridge output signal that is double in magnitude. Thus, hot wires $R_1$ and $R_2$ serve to generate a flow measurement signal, and hot wires $R_3$ and $R_4$ serve as bridge balancing resistors.

When the described apparatus is employed as an anemometer, the gas whose velocity or flow rate is to be measured is supplied to conduit 70, passes through cavities 11 and 12, and is vented to the atmosphere through conduits 71 and 72. The higher the gas flow rate through cavities 11 and 12, the more hot wires $R_1$ and $R_2$ are cooled and the greater is the reduction in resistance thereof, designated ΔR in FIG. 5. There are no fluid entrances to, nor exits from, cavities 13 and 14. The resistance of the hot wires in these cavities, however, changes as a function of ambient temperature in the same manner as hot wires $R_1$ and $R_2$. Consequently, the effect of temperature changes are balanced by the bridge.

Figure 6:
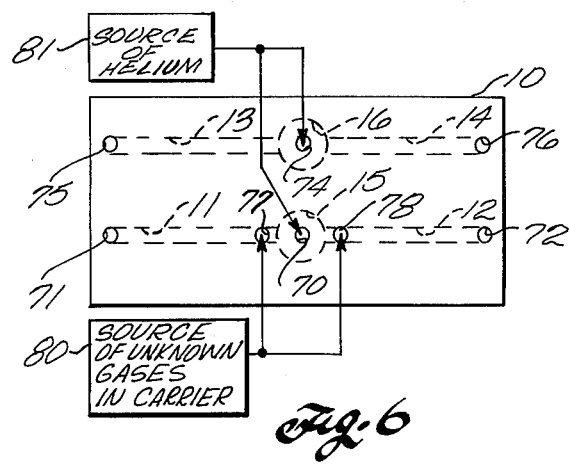
FIG. 6 is a top plan view of the apparatus of FIG. 1 adapted for chromatography with gas sources shown in block form.

When the described apparatus is employed in chromatography, one or more unknown gases flow through cavities 11 and 12, and a reference gas, which is usually helium because of its high thermal conductivity, flows through cavities 13 and 14. FIG. 6 shows the apparatus in this application. Housing 10 has an entrance conduit 74 to chamber 16, an exit conduit 75 from the end of cavity 13 opposite chamber 16, and an exit conduit 76 from the end of cavity 14 opposite chamber 16. Conduits 71, 72, 75 and 76 could vent to the atmosphere or a fluid receiver. Housing 10 has an entrance conduit 77 to cavity 11 for unknown gases near chamber 15 and an entrance conduit 78 to cavity 12 for unknown gases near chamber 15. If the unknown gases were supplied to entrance conduit 70, the large cross section of chamber 15 relative to cavities 11 and 12 would spread the pulses generated by the bridge responsive to such unknown gases and merge successive pulses. This undesirable result is averted by supplying the unknown gases directly to cavities 11 and 12 via entrance conduits 77 and 78. As shown schematically in FIG. 6, the source of one or more unknown gases in a carrier, preferably helium, is connected to entrance conduits 77 and 78. The unknown gases are separated from each other and interleaved with the carrier gas in a manner well known in the art and therefore not disclosed herein. A source of reference gas, preferably helium, is connected to entrance conduit 74 for the purpose of cooling hot wires $R_3$ and $R_4$, and is connected to entrance conduit 70 for the purpose of preventing gas from source 80 from flowing to chamber 15. Therefore, the unknown gases in the carrier flow in their entirety from entrance conduits 77 and 78 through cavities 11 and 12 respectively to exit conduits 71 and 72 respectively. Accordingly, sharp, well separated pulses are generated by the bridge in response to the unknown gases of source 80.

The described embodiments of the invention are only considered to be preferred and illustrative of the inventive concept; the scope of the invention is not to be restricted to such embodiments. Various and numerous other arrangements may be devised by one skilled in the art without departing from the spirit and the scope of this invention. For example, hot wires $R_1$ and $R_2$ could be placed in separate cavities if desired, though this has not been found necessary to date. Further, the various features of the invention could be practiced separately if desired—the pair of rods disclosed herein could be substituted for the single rod in my above-referenced patent or a single rod could be employed in the arrangement disclosed herein. Further, if the sensitivity provided by a hot wire in each arm of the bridge is not required, hot wires could be employed in only two of the four arms.

I claim:

1. Fluid measuring apparatus comprising:
    a housing having an elongated cavity enclosed on its sides;
    a first thin elongated hot wire bent in half to extend along the length of the cavity away from a junction;
    a second thin elongated hot wire bent in half to extend along the length of the cavity away from the junction;
    first means at the junction for supporting the ends of each hot wire in spaced electrically isolated relationship from each other and connecting one end of the first and second hot wires to each other to form in effect a first single hot wire equal in length to the first and second hot wires;
    second means spaced along the length of the cavity from the junction for supporting the middle of the first hot wire to exert tension thereon as the length of the first hot wire changes;
    third means spaced along the length of the cavity from the junction for supporting the middle of the second hot wire to exert tension thereon as the length of the second hot wire changes;
    means for forming in the housing a fluid entrance to the cavity;
    means for forming in the housing a fluid exit from the cavity longitudinally spaced from the entrance so the hot wires lie between the entrance and the exit; and
    means for measuring the change in resistance of the hot wires.

2. The apparatus of claim 1, in which the junction is centrally located relative to the ends of the cavity, the first hot wire extends in one direction from the junction, the second hot wire extends in the opposite direction from the junction, the second supporting means is located near one end of the cavity, and the third supporting means is located near the other end of the cavity.

3. The apparatus of claim 2, in which the first supporting means supports the ends of each of the first and second hot wires in fixed relationship longitudinally and laterally with respect to each other.

4. The apparatus of claim 3, in which the first supporting means comprises a printed circuit board having a first electrically conductive pad to which one end of each of the first and second hot wires is soldered, a second electrically conductive pad to which the other end of the first hot wire is soldered, and a third electrically conductive pad to which the other end of the second hot wire is soldered, the pads being electrically isolated from each other.

5. The apparatus of claim 4, in which the circuit board is circular and the pads are arcuate and concentric.

6. The apparatus of claim 5, in which the second and third supporting means each comprise a pair of closely spaced rods around which the middle of the respective hot wires are wrapped, the rod pairs being deformed to exert tension on the respective hot wires to keep the corresponding hot wires taut as their length changes.

7. The apparatus of claim 6, in which the rods are spaced to support the halves of the corresponding hot wire parallel to each other.

8. The fluid measuring apparatus of claim 7, additionally comprising:
    a third thin elongated hot wire bent in half to extend along the length of the cavity away from the junction;
    a fourth thin elongated hot wire bent in half to extend along the length of the cavity away from the junction in the opposite direction from the third hot wire;
    fourth means at the junction for supporting the ends of each of the third and fourth hot wires in spaced electrically isolated relationship from each other and from the first and second hot wires, and electrically connecting one end of the third and fourth hot wires to each other to form in effect a second single hot wire equal in length to the third and fourth hot wires;

fifth means spaced along the length of the cavity from the junction for supporting the middle of the third hot wire to exert tension thereon as the length of the third hot wire changes;

sixth means spaced along the length of the cavity from the junction for supporting the middle of the fourth hot wire to exert tension thereon as the length of the fourth hot wire changes;

a source of electrical excitation energy having first and second output terminals;

first and second bridge balancing resistors;

means for connecting the first single hot wire and the first resistor in series with the first single hot wire connected to the first output terminal and the first resistor connected to the second output terminal; and means for connecting the second single hot wire and the second resistor in series with the second single hot wire connected to the second output terminal and the second resistor connected to the first output terminal, whereby the first and second single hot wires and the first and second resistors form a bridge having an output between the junction of the first single hot wire and the first resistor and the junction of the second single hot wire and the second resistor.

9. The apparatus of claim 8 additionally comprising:

a chamber wider than the first cavity, the circuit board being located in the chamber and the means for forming a fluid entrance comprising a first conduit leading to the chamber and a second conduit leading to the cavity near the chamber;

a source of one or more unknown gases in a carrier gas;

means for connecting the source to the second conduit; and means for coupling the carrier gas without unknown gases to the first conduit to prevent the one or more unknown gases from flowing to the chamber.

10. The apparatus of claim 1, in which the second and third supporting means each comprise a pair of closely spaced rods around which the middle of the respective hot wires are wrapped, the rod pairs being deformed to exert tension on the respective hot wires to keep the corresponding hot wires taut as their length changes.

11. The apparatus of claim 1, additionally comprising:

a chamber wider than the first cavity at the junction, the means for forming a fluid entrance comprising a first conduit leading to the chamber and a second conduit leading to the cavity near the chamber;

a source of one or more unknown gases in a carrier gas;

means for connecting the source to the second conduit; and means for coupling the carrier gas without unknown gases to the first conduit to prevent the one or more unknown gases from flowing to the chamber.

12. The fluid measuring apparatus of claim 2, additionally comprising:

a third thin elongated hot wire bent in half to extend along the length of the cavity away from the junction;

a fourth thin elongated hot wire bent in half to extend along the length of the cavity away from the junction in the opposite direction from the third hot wire;

fourth means at the junction for supporting the ends of each of the third and fourth hot wires in spaced electrically isolated relationship from each other and from the first and second hot wires, and electrically connecting one end of the third and fourth hot wires to each other to form in effect a second single hot wire equal in length to the third and fourth hot wires;

fifth means spaced along the length of the cavity from the junction for supporting the middle of the third hot wire to exert tension thereon as the length of the third hot wire changes;

sixth means spaced along the length of the cavity from the junction for supporting the middle of the fourth hot wire to exert tension thereon as the length of the fourth hot wire changes;

a source of electrical excitation energy having first and second output terminals;

first and second bridge balancing resistors;

means for connecting the first single hot wire and the first resistor in series with the first single hot wire connected to the first output terminal and the first resistor connected to the second output terminal; and means for connecting the second single hot wire and the second resistor in series with the second single hot wire connected to the second output terminal and the second resistor connected to the first output terminal, whereby the first and second single hot wires and the first and second resistors form a bridge having an output between the junction of the first single hot wire and the first resistor and the junction of the second single hot wire and the second resistor.

13. The apparatus of claim 12, in which the first resistor comprises:

a second elongated cavity enclosed on its sides in the housing;

a fifth thin elongated hot wire bent in half to extend along the length of the second cavity away from a second junction centrally located relative to the ends of the second cavity;

a sixth thin elongated hot wire bent in half to extend along the length of the second cavity away from the second junction in the opposite direction from the fifth hot wire;

seventh means at the second junction supporting the ends of each of the fifth and sixth hot wires in spaced electrically isolated relationship from each other and electrically connecting one end of the fifth and sixth hot wires to each other to form in effect as the first resistor a single hot wire equal in length to the fifth and sixth hot wires;

eighth means spaced along the length of the second cavity from the second junction for supporting the middle of the fifth hot wire to exert tension thereon as the length of the fifth hot wire changes; and ninth means spaced along the length of the second cavity from the second junction for supporting the middle of the sixth hot wire to exert tension thereon as the length of the sixth hot wire changes;

and the second resistor comprises:
- a seventh thin elongated hot wire bent in half to extend along the length of the second cavity away from the second junction;
- an eighth thin elongated hot wire bent in half to extend along the length of the second cavity away from the second junction in the opposite direction from the seventh hot wire;
- tenth means at the second junction for supporting the ends of each of the seventh and eighth hot wires in spaced electrically isolated relationship from each other and from the fifth and sixth hot wires, and, electrically connecting one end of the seventh and eighth hot wires to each other to form in effect as the second resistor a single hot wire equal in length to the seventh and eighth hot wires;
- eleventh means spaced along the length of the second cavity from the second junction for supporting the middle of the seventh hot wire to exert tension thereon as the length of the seventh hot wire changes; and
- twelfth means spaced along the length of the second cavity from the second junction for supporting the middle of the eighth hot wire to exert tension thereon as the length of the eighth hot wire changes.

14. The apparatus of claim 12, in which the first and fourth supporting means comprise a printed circuit board having on one surface a first electrically conductive pad to which one end of each of the first and second hot wires is soldered, a second electrically conductive pad to which one end of the first hot wire is soldered, a third electrically conductive pad to which the other end of the second hot wire is soldered, a fourth electrically conductive pad to which one end of each of the third and fourth hot wires is soldered, a fifth electrically conductive pad to which the other end of the third hot wire is soldered, and a sixth electrically conductive pad to which the other end of the fourth hot wire is soldered, the pads being electrically isolated from each other.

15. The apparatus of claim 14, in which the printed circuit board is circular, the pads are arcuate and concentric, and the first and fourth pads surround the second, third, fifth, and sixth pads.

16. The apparatus of claim 15, additionally comprising seventh, eighth, ninth, and tenth mutually isolated pads on the surface of the printed circuit board opposite the one surface and plated through holes connecting the second, third, fifth, and sixth pads respectively with the seventh, eighth, ninth, and tenth pads.

17. Fluid measuring apparatus comprising:
- a housing having an elongated cavity enclosed on its sides;
- a thin elongated hot wire bent in half to extend along the length of the cavity;
- means at one area of the cavity for supporting the ends of the hot wire in closely spaced, electrically isolated relationship from each other;
- first and second closely spaced rods at another area of the cavity spaced from the one area to support the middle of the wire, the middle of the wire being wrapped around the rods and the rods being deformed to exert tension on the hot wire to keep the hot wire taut as its length changes;
- means for maintaining the spacing of the first and second rods;
- means for forming in the housing a fluid entrance to the cavity;
- means for forming in the housing a fluid exit from the cavity longitudinally spaced from the entrance so the hot wire lies between the entrance and the exit; and
- means for measuring the change in resistance of the hot wire.

18. The fluid measuring apparatus of claim 17, in which the rods are spaced apart a distance to maintain the halves of the hot wire in parallel relationship.

19. Gas chromatographic apparatus comprising:
- a housing having a first elongated cavity and a second elongated cavity;
- a chamber at one end of the first cavity having a cross section larger in area than the first cavity;
- a first thin elongated hot wire extending along the length of the first cavity;
- first means in the chamber for supporting the first hot wire in spaced relationship from the sides of the cavity;
- second means at an area of the cavity spaced from the chamber for supporting the first hot wire in spaced relationship from the sides of the cavity;
- means for forming in the housing a fluid entrance to the chamber;
- means for forming in the housing near the chamber a fluid entrance to the first cavity;
- means for forming in the housing a fluid exit from the first cavity longitudinally spaced from the entrance to the first cavity so the hot wire lies between the entrance to the first cavity and the exit from the first cavity;
- a second thin elongated hot wire supported to extend along the length of the second cavity in spaced relationship from the sides thereof;
- means for forming in the housing a fluid entrance to the second cavity;
- means for forming in the housing a fluid exit from the second cavity longitudinally spaced from the entrance to the second cavity so the hot wire lies between the entrance to the second cavity and the exit from the second cavity;
- a source of one or more unknown gases in a carrier of reference gas coupled to the entrance to the first cavity;
- a source of reference gas coupled to the entrance to the second cavity;
- means for coupling a reference gas to the chamber to prevent the one or more unknown gases in a carrier from flowing to the chamber; and
- means for measuring the difference in the change in resistance of the first and second hot wires responsive to the reference gas and the one or more unknown gases in a carrier.

* * * * *